(12) United States Patent
Park et al.

(10) Patent No.: US 9,126,366 B2
(45) Date of Patent: Sep. 8, 2015

(54) APPARATUS AND METHOD FOR MANUFACTURING CELL CULTURE SCAFFOLD

(75) Inventors: Su A Park, Daejeon (KR); Wan-Doo Kim, Daejeon (KR); Junhee Lee, Daejeon (KR)

(73) Assignee: KOREA INSTITUTE OF MACHINERY & MATERIALS, Daejeon (KR)

( * ) Notice: Subject to any disclaimer, the term of this patent is extended or adjusted under 35 U.S.C. 154(b) by 673 days.

(21) Appl. No.: 13/160,577

(22) Filed: Jun. 15, 2011

(65) Prior Publication Data
US 2012/0322154 A1  Dec. 20, 2012

(51) Int. Cl.
*C12N 5/071* (2010.01)
*C12M 3/00* (2006.01)
*B29C 67/00* (2006.01)

(52) U.S. Cl.
CPC .................. *B29C 67/0059* (2013.01)

(58) Field of Classification Search
CPC  B29C 67/0085; B29C 67/0059; B33Y 10/00; B33Y 30/00
USPC ................. 425/375, 174.8 E, 174.8 R, 324.1; 264/465; 435/395, 283.1
See application file for complete search history.

(56) References Cited

U.S. PATENT DOCUMENTS

| | | | | |
|---|---|---|---|---|
| 1,886,026 A * | 11/1932 | Kellems | ........................ | 403/373 |
| 2,116,942 A * | 5/1938 | Formhals | ........................ | 264/10 |
| 3,539,128 A * | 11/1970 | Chambon | ................... | 242/573.6 |
| 4,405,931 A * | 9/1983 | Fujisawa | ................... | 346/139 R |
| 5,529,471 A * | 6/1996 | Khoshevis | ..................... | 425/112 |
| 6,612,824 B2 * | 9/2003 | Tochimoto et al. | ............ | 425/130 |
| 6,905,645 B2 * | 6/2005 | Iskra | .............................. | 264/128 |
| 7,074,276 B1 * | 7/2006 | Van Sciver et al. | ........... | 118/500 |
| 7,083,697 B2 | 8/2006 | Dao et al. | | |
| 7,105,124 B2 * | 9/2006 | Choi | ............................. | 264/465 |
| 7,575,707 B2 * | 8/2009 | Xia et al. | ...................... | 264/465 |
| 7,615,373 B2 | 11/2009 | Simpson et al. | | |
| 7,625,198 B2 | 12/2009 | Lipson et al. | | |
| 7,625,200 B2 * | 12/2009 | Leavitt | .......................... | 425/375 |
| 7,640,789 B2 * | 1/2010 | Kim et al. | ..................... | 73/31.06 |
| 7,661,541 B2 * | 2/2010 | Dao et al. | ................. | 210/500.22 |
| 7,759,082 B2 | 7/2010 | Bowlin et al. | | |
| 7,824,601 B1 * | 11/2010 | Stankus et al. | ................ | 264/465 |
| 7,939,003 B2 | 5/2011 | Bonassar et al. | | |
| 7,980,838 B2 * | 7/2011 | Park | ............................. | 425/83.1 |
| 7,981,353 B2 * | 7/2011 | Mitchell et al. | ............... | 264/465 |
| 8,263,187 B2 | 9/2012 | Kitazono et al. | | |
| 8,293,530 B2 | 10/2012 | Burgess et al. | | |
| 8,529,956 B2 | 9/2013 | Campbell et al. | | |

(Continued)

FOREIGN PATENT DOCUMENTS

KR   1020020059382   7/2002
KR   1020050093176   9/2005

(Continued)

*Primary Examiner* — Nahida Sultana
(74) *Attorney, Agent, or Firm* — Lexyoume IP Meister, PLLC

(57) ABSTRACT

A cell culture scaffold manufacturing apparatus according to an exemplary embodiment of the present invention includes a solution storage portion in which a biopolymer solution is stored; a plotter that includes a plotter nozzle for ejecting a solution supplied from the solution storage portion; and a cylindrical collection portion that has a cylinder shape and is disposed at a lower portion of the plotter so that the solution ejected through the plotter nozzle of the plotter is collected.

6 Claims, 13 Drawing Sheets

(56) References Cited

U.S. PATENT DOCUMENTS

| | | |
|---|---|---|
| 8,529,958 B2 | 9/2013 | Campbell et al. |
| 8,529,959 B2 | 9/2013 | Campbell et al. |
| 8,529,960 B2 | 9/2013 | Campbell et al. |
| 8,529,961 B2 | 9/2013 | Campbell et al. |
| 8,586,345 B2 | 11/2013 | Simpson et al. |
| 8,636,938 B2 | 1/2014 | Bonassar et al. |
| 2002/0090725 A1* | 7/2002 | Simpson et al. ............. 435/402 |
| 2004/0004303 A1* | 1/2004 | Iskra ............................ 264/109 |
| 2006/0216320 A1 | 9/2006 | Kitazono |
| 2007/0170140 A1* | 7/2007 | Gaunekar et al. ............ 212/312 |
| 2007/0254001 A1 | 11/2007 | Kim et al. |
| 2008/0102098 A1* | 5/2008 | Dave et al. ................... 424/426 |
| 2008/0105593 A1 | 5/2008 | Kleinsmith |
| 2008/0159985 A1 | 7/2008 | Bowlin et al. |
| 2009/0035449 A1* | 2/2009 | Chen et al. .................. 427/2.25 |
| 2009/0208577 A1* | 8/2009 | Xu et al. ....................... 424/484 |
| 2009/0324671 A1* | 12/2009 | Ngo et al. .................... 424/423 |
| 2010/0014747 A1* | 1/2010 | Freifeld ........................ 382/141 |
| 2010/0034960 A1* | 2/2010 | Kindaichi et al. ........... 427/2.25 |
| 2010/0127433 A1* | 5/2010 | Medina et al. ................ 264/401 |
| 2010/0219563 A1* | 9/2010 | Chang et al. .................. 264/465 |
| 2010/0254900 A1 | 10/2010 | Campbell |
| 2010/0310658 A1 | 12/2010 | Bowlin et al. |
| 2011/0074065 A1* | 3/2011 | Batchelder et al. ........... 264/308 |
| 2011/0139653 A1 | 6/2011 | Kleinsmith |
| 2011/0280841 A1 | 11/2011 | Bowlin et al. |
| 2011/0287122 A1* | 11/2011 | Kim et al. .............. 425/174.8 R |
| 2011/0288026 A1* | 11/2011 | Simpson et al. .............. 514/17.2 |
| 2013/0035753 A1* | 2/2013 | Chen et al. ................... 623/1.16 |
| 2013/0089642 A1 | 4/2013 | Lipson et al. |
| 2013/0189370 A1 | 7/2013 | Campbell et al. |
| 2014/0117586 A1 | 5/2014 | Bonassar et al. |

FOREIGN PATENT DOCUMENTS

| | | |
|---|---|---|
| KR | 1020050120687 | 12/2005 |
| KR | 1020090052756 | 5/2009 |
| WO | 03/079985 | 10/2003 |
| WO | 2004/061177 | 7/2004 |
| WO | 2006/020685 | 2/2006 |
| WO | 2008/057436 | 5/2008 |

* cited by examiner (a)

(b)

(c)

(d)

APPARATUS AND METHOD FOR MANUFACTURING CELL CULTURE SCAFFOLD

BACKGROUND OF THE INVENTION (a) Field of the Invention

The present invention relates to a cell culture scaffold manufacturing apparatus, a method for manufacturing a cell culture scaffold by using the apparatus.

(b) Description of the Related Art

A tissue engineering means that a necessary tissue is sampled from a body of a patient, a cell is separated from a tissue specimen thereof, and the separated cell is proliferated by a necessary amount through culturing, implanted in a porous biodegradable polymer scaffold, and in vitro cultured for a predetermined period of time, and a hybrid type cell culture scaffold is transplanted into a human body.

A method where after the transplantation, in the case of most tissues or viscera, the cell is supplied with oxygen and nutrition by diffusion of a secretion until a novel vascular is formed, and if supplying of blood is implemented by providing the vascular to the human body, novel tissue and viscera are formed by proliferation and division of the cell while the polymer scaffold is degraded and removed is applied.

Accordingly, in order to study this tissue engineering, first, it is important to manufacture a biodegradable polymer cell culture scaffold similar to a biological tissue.

A main factor of a material of a scaffold used in order to regenerate a human body tissue has mechanical strength sufficiently acting as a substrate or a scaffold so as to form a tissue having a three dimensional structure by attaching the tissue cell to the material surface and acts as an intermediate barrier positioned between the transplanted cell and a host cell, and to this end, after the transplantation, non-toxic biocompatibility where blood coagulation or inflammation reaction does not occur is required.

In addition, if the transplanted cell acts as a novel internal tissue, the material should have a biodegradability so that the cell is completely degraded and removed in the body within a desired time.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide a cell culture scaffold manufacturing apparatus that can manufacture more various types of cell culture scaffolds including a cylinder shape which is difficult to be manufactured by a known apparatus by using a cylindrical collection portion, and particularly, can be easily used in a vascular, a nervous conduit, or a trachea, and a cell culture scaffold manufactured by using the apparatus.

Further, the present invention has been made in an effort to provide a cell culture scaffold manufacturing apparatus that can easily form a cell culture scaffold, easily implement nanofibers collected between the cell culture scaffolds by using a single device, reduce a manufacturing time by simultaneously moving a plotter and an electrospinning unit, and improve cell proliferation efficiency by forming a nano-scale cell culture scaffold, and a cell culture scaffold manufactured by using the apparatus.

In addition, the present invention has been made in an effort to provide a method for manufacturing a cell culture scaffold manufactured by supplying a drug when the cell culture scaffold is manufactured.

Moreover, the present invention has been made in an effort to provide a plotter apparatus manufactured by supplying a drug when the cell culture scaffold is manufactured.

An exemplary embodiment of the present invention provides a cell culture scaffold manufacturing apparatus, including: a solution storage portion in which a biopolymer solution is stored; a plotter that includes a plotter nozzle for spraying a solution supplied from the solution storage portion; and a cylindrical collection portion that has a cylinder shape and is disposed at a lower portion of the plotter so that the solution sprayed through the plotter nozzle of the plotter is collected.

The cell culture scaffold manufacturing apparatus may further includes a first position control portion that controls a spraying position by moving the plotter in an x-y-z axis direction; a second position control portion that controls a position at which the solution is collected by controlling a rotation speed of the cylindrical collection portion; and a controller controlling the first position control portion and the second position control portion.

The first position control portion may includes a support bracket supporting the plotter and including a z-axis guiderail for moving the plotter in a z-axis direction; a x-axis guiderail and y-axis guiderail moving the support bracket in a x-axis and a y-axis, respectively.

The second position control portion may includes a fixing shaft fixing the cylindrical collection portion and a driver rotating the fixing shaft, and the cylindrical collection portion is detachably formed in the fixing shaft by forming a hollow portion into which the fixing shaft is inserted at both ends in a central axis direction.

The fixing shaft may includes a position determination protrusion portion in which a portion of an external circumferential surface is protruded to determine a collection position of the cylindrical collection portion, and a hollow region of the hollow portion is enlarged so that the position determination protrusion portion is inserted thereinto.

When the solution storage portion is a first solution storage portion, the cell culture scaffold manufacturing apparatus may further includes an electrospinning unit that includes a second solution storage portion in which a biopolymer solution is stored, an electrospinning nozzle that sprays a solution supplied from the second solution storage portion, and a voltage generation portion applying a voltage to the electrospinning nozzle and the cylindrical collection portion, and nanofibers are discharged between the cell culture scaffolds formed through the plotter by using the electrospinning unit.

A spraying position may be controlled by the first position control portion by fixing the electrospinning unit by the support bracket.

The plotter may include a first plotter nozzle and a second plotter nozzle having divided regions, and the cell culture scaffold manufacturing apparatus further includes a drug storage portion connected to the first plotter nozzle through the first supply tube, and the solution storage portion connected to the second plotter nozzle through the second supply tube.

The second plotter nozzle may surround an external side of the first plotter nozzle in a length direction and have a ring-shaped tube.

An additive storage portion connected through the first plotter nozzle and the third supply tube may be further included.

Another exemplary embodiment of the present invention provides a cell culture scaffold manufacturing apparatus including: a plotter including a first plotter nozzle and a second plotter nozzle having divided regions; a drug storage portion connected with the first plotter nozzle through the first supply tube and storing a drug; and a solution storage portion connected with the second plotter nozzle through the second supply tube and storing a biopolymer solution.

The second plotter nozzle may surround an external side of the first plotter nozzle in a length direction and have a ring-shaped tube.

The cell culture scaffold manufacturing apparatus may further includes an additive storage portion connected with the first plotter nozzle through the third supply tube.

The cell culture scaffold manufacturing apparatus may further include a base frame in which a lower plate and straight type y-axis guiderail supports that are separated from each other at both ends of the lower plate to protrude are provided, and a collection table is installed between the y-axis guiderail supports; y-axis guiderails installed on the y-axis guiderail supports; an x-axis guiderail support on which an x-axis guiderail is installed and which is mounted on the y-axis guiderails and moved in an y-axis direction; a support bracket mounted on the x-axis guiderail and moved in the x-axis direction; a z-axis guiderail support which is fixed and installed in the support bracket and on which a z-axis guiderail is installed; and a z-axis moving bracket which is mounted on the z-axis guiderail and moved in a z-axis direction and on which a drug storage portion, a solution storage portion and a plotter are fixed and installed.

The cell culture scaffold manufacturing apparatus may further includes an additive storage portion fixed on the z-axis moving bracket.

The cell culture scaffold according to the exemplary embodiment of the present invention may be manufactured by using the above cell culture scaffold manufacturing apparatus, and the cell culture scaffold may be used for a vascular, a nervous conduit, or a trachea, and used for a stent.

Yet another exemplary embodiment of the present invention provides a method for manufacturing a cell culture scaffold including: supplying a drug that promotes a cell growth to a drug storage portion, supplying a biopolymer solution used as a scaffold to a solution storage portion, and supplying an water-soluble or biodegradable material for generating a pore to the solution storage portion; and providing the drug through the first supply tube into the first plotter nozzle, providing the biopolymer solution and the water-soluble or biodegradable material through the second supply tube into the second plotter nozzle, and performing plotting by using a plotter.

Still yet another exemplary embodiment of the present invention provides a method for manufacturing a cell culture scaffold including: supplying a drug that promotes a cell growth to a drug storage portion; supplying a biopolymer solution used as a scaffold to a solution storage portion; supplying a water-soluble or biodegradable material for generating a pore to the additive storage portion; and providing the drug through the first supply tube into the first plotter nozzle, providing the biopolymer solution and the water-soluble or biodegradable material through the second supply tube into the second plotter nozzle, providing the water-soluble or biodegradable material through a third supply tube into a third plotter nozzle, and performing plotting by using a plotter.

The drug may be a growth factor, cytokine, an antibiotic or an antimicrobial.

The growth factor may be a bone morphogenetic protein (BMP), a cell proliferation suppress factor (TGF-β), an insulin-like growth factor (IGF), a fibroblast growth factor (FGF), a platelet-derived growth factor (PDGF), keratinocyte cell growth factor (KGF) or an epidermal growth factor (EGF).

The cytokine may be interleukin-2, interferon-α (IFN-α) or interferon-β (IFN-β).

The antibiotic may be one or more selected from the group consisting of penicillin, streptomycin, kanamycin, neomycin, bacitracin, gentamycin and vancomycin.

The antimicrobial may be amphotericin-B, nystatin, or polymixin.

The biopolymer solution may be one or more selected from the group consisting of polycaprolactone, polylactide, polyglycolide, and polydioxanone.

The water-soluble material may be a salt solution, sucrose, polyethylene oxide (PEO) or polyvinyl alcohol (PVA).

The biodegradable material may be a polyglycolic acid, polycaprolactone, polylactic acid or polydioxanone.

According to exemplary embodiments of the present invention, there are merits in that a cell culture scaffold manufacturing apparatus and a cell culture scaffold manufactured by using the apparatus according to an exemplary embodiment of the present invention can manufacture more various types of cell culture scaffolds including a cylinder shape, semicircular shape, and the like which is difficult to be manufactured by a known apparatus by using a cylindrical collection portion, and particularly, can be easily used in all cylindrical human tissues such as a vascular, a nervous conduit, or a trachea and medical goods such as a stent.

In addition, there are merits in that a cell culture scaffold manufacturing apparatus and a cell culture scaffold manufactured by using the apparatus according to an exemplary embodiment of the present invention can easily form the cell culture scaffold by using a plotter for spraying a solution in which a biodegradable material is dissolved or melted, form a nano-level cell culture scaffold by forming an electrospinning unit for electrically discharging the biopolymer solution in the apparatus and performing simultaneous moving, increase manufacturing efficiency by reducing a manufacturing time, and improve cell proliferation efficiency.

A method for manufacturing a cell culture scaffold according to the exemplary embodiments of the present invention can manufacture a cell culture scaffold formed of a drug and a synthetic polymer by using a plotter apparatus at a time, supply the drug to a cell by adding a water-soluble or biodegradable material, and control a drug efflux, such that the method may be easily used in manufacturing of the cell culture scaffold.

DETAILED DESCRIPTION OF THE EMBODIMENTS

Figure 1:
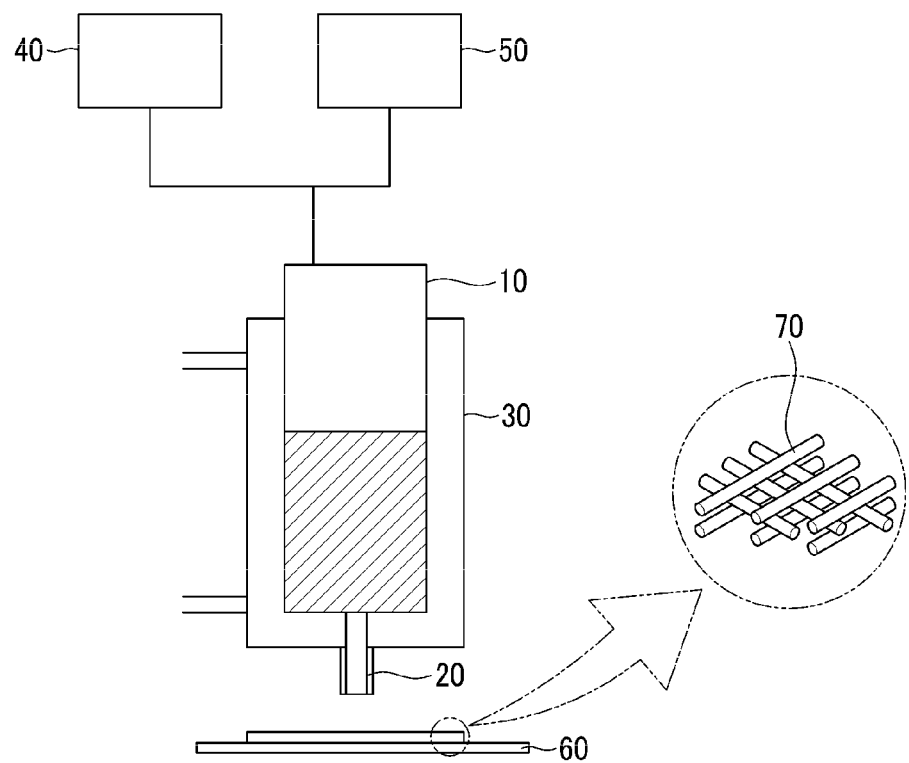
FIG. 1 is a schematic diagram illustrating a basic driving notion of a cell culture scaffold manufacturing apparatus.

Exemplary embodiments of the present invention will be described more fully hereinafter with reference to the accompanying drawings, in which exemplary embodiments of the invention are shown. As those skilled in the art would realize, the described embodiments may be modified in various different ways, all without departing from the scope of the present invention.

The drawings and description are to be regarded as illustrative in nature and not restrictive. Like reference numerals designate like elements throughout the specification.

FIG. 1 is a schematic diagram illustrating a basic driving notion of a cell culture scaffold manufacturing apparatus.

The cell culture scaffold manufacturing apparatus shown in FIG. 1 includes a cartridge 10 in which a nozzle 20 is formed at a lower portion thereof and a material for forming a cell culture scaffold 70 is included therein, a temperature control means 30 for maintaining a material for forming the cell culture scaffold 70 in the cartridge 10 at a predetermined temperature, a moving means 40 for moving the cartridge 10 in upward, downward, left, and right directions, a pressurizing means 50 applying a pressure into the cartridge 10 so that the material for forming the cell culture scaffold 70 in the cartridge 10 is sprayed, and a collection portion 60 collecting the material for forming the cell culture scaffold 70 ejected through the nozzle 20.

The cell culture scaffold 70 forms a cell culture scaffold 70 having a predetermined structure by controlling a plotting position of the material for forming the cell culture scaffold through the moving means 40.

Figure 2:
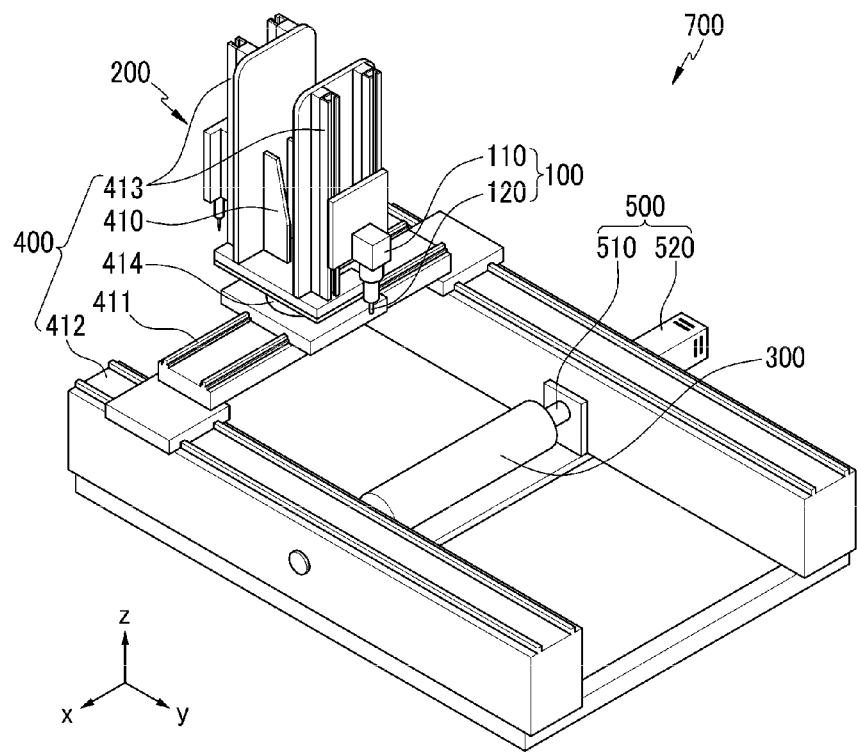
FIG. 2 is a perspective view that illustrates a cell culture scaffold manufacturing apparatus according to a first exemplary embodiment of the present invention.
Figure 3:
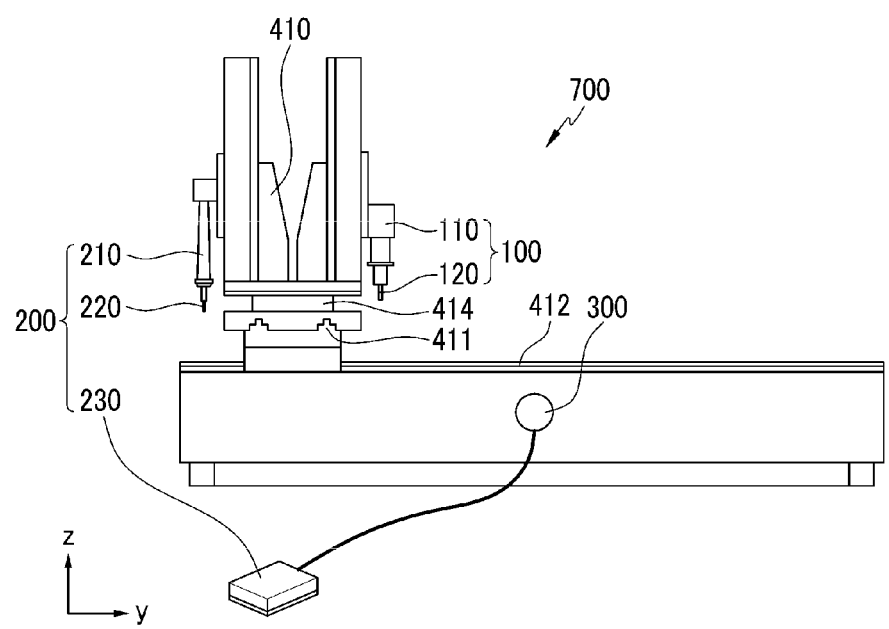
FIG. 3 is a side view that illustrates a cell culture scaffold manufacturing apparatus according to the first exemplary embodiment of the present invention.
Figure 4:
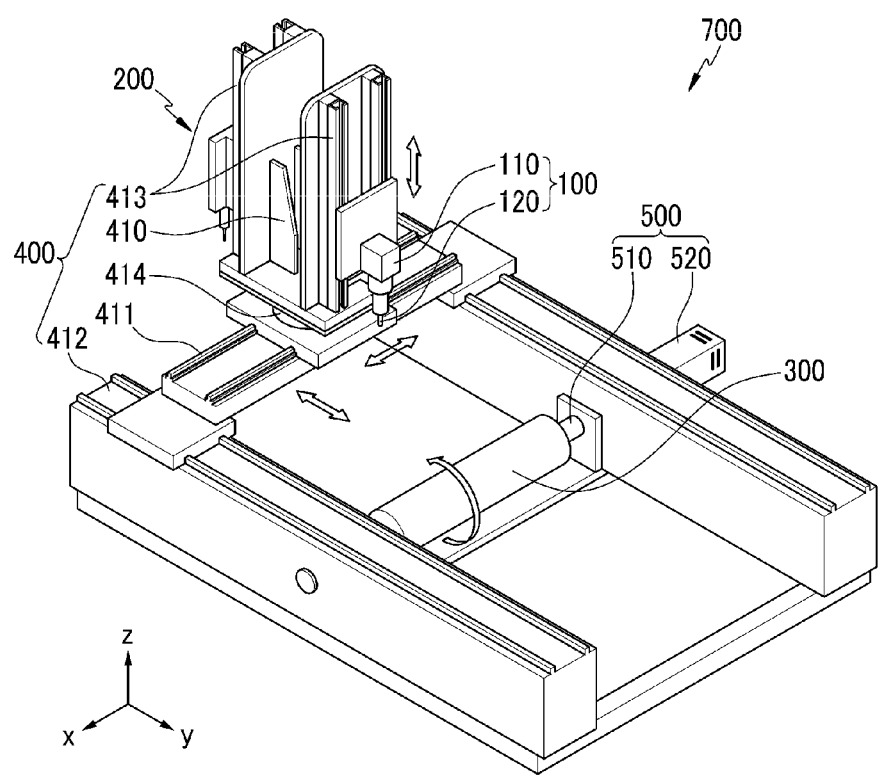
FIG. 4 is a schematic view that illustrates operation of a cell culture scaffold manufacturing apparatus according to the first exemplary embodiment of the present invention.

FIGS. 2 to 4 are a perspective view, a side view, and a schematic view that illustrates operation of a cell culture scaffold manufacturing apparatus 700 according to a first exemplary embodiment of the present invention.

The cell culture scaffold manufacturing apparatus 700 according to the exemplary embodiment includes a plotter 100 and a cylindrical collection portion 300.

The plotter 100 is a means for ejecting a biopolymer solution forming the cell culture scaffold, and includes the first solution storage portion 110 storing the biopolymer solution in which the biodegradable material is dissolved or melted and a plotter nozzle 120 ejecting the solution supplied from the first solution storage portion 110.

The cylindrical collection portion 300 is provided at a lower portion of the plotter 100 so that the cell culture scaffold is formed by collecting the solution ejected from the plotter nozzle 120.

The plotter 100 can be moved, and in the exemplary embodiment, the provision of the cylindrical collection portion 300 at the lower side of the plotter 100 means that the cylindrical collection portion 300 is positioned beneath the plotter 100 in a height direction (z-axis direction in FIG. 2).

There are merits in that the cell culture scaffold manufacturing apparatus 700 of the exemplary embodiment can form the cylindrical cell culture scaffold that is difficult to be manufactured by using a known apparatus by forming the cylindrical collection portion 300 for forming the cell culture scaffold, and can manufacture various types of cell culture scaffold including a hemisphere.

The cylindrical collection portion 300 as a basic framework for forming the cell culture scaffold, may be formed of metal such as stainless steel or resin.

In another embodiment, the cylindrical collection portion 300 may be formed of a material that is easily removed in order to easily separate the cylindrical collection portion after the cell culture scaffold is formed.

In more detail, the cylindrical collection portion 300 may be formed of a material that deformation of a shape or a cutting is easy, or a material that can be dissolved in a predetermined solvent, and the cell culture scaffold manufacturing apparatus 700 according to the exemplary embodiment of the present invention may be formed of various materials that has a predetermined shape so as to form the cell culture scaffold and is easily removed.

The shape of the cell culture scaffold that can be manufactured through the cell culture scaffold manufacturing apparatus 700 of the exemplary embodiment will be again described below.

The cell culture scaffold manufacturing apparatus 700 of the exemplary embodiment may further include an electrospinning unit 200, and the electrospinning unit 200 is a means electrospinning nanofibers in a fiber thread between the basic frameworks of the cell culture scaffolds formed by ejecting the solution through the plotter 100 and on the surface thereof.

In more detail, the electrospinning unit 200 includes a second solution storage portion 210 storing the biopolymer solution, an electrospinning nozzle 220 electrospinning the solution supplied from the second solution storage portion 210, and a voltage generation portion 230 applying a voltage to the electrospinning nozzle 220 and cylindrical collection portion 300 (refer to FIG. 3).

In this case, the plotter 100 and the electrospinning unit 200 should form the cell culture scaffold having a predetermined shape by moving, and the cell culture scaffold manufacturing apparatus 700 of the exemplary embodiment includes a plotting position control portion 400 controlling the plotting position by moving the plotter 100 and the electrospinning unit 200 in an x-y-z axis direction.

The plotting position control portion 400 is a means for moving the plotter 100 and the electrospinning unit 200 in the x-y-z axis direction, and the plotter 100 and the electrospinning unit 200 may be installed in one support bracket 410 because of means performing continuous discharging.

That is, in the plotting position control portion 400, the plotter 100 and the electrospinning unit 200 are fixed to the support bracket 410, and a z-axis guiderail 413 is formed so as to move in the z-axis direction.

In addition, the plotting position control portion 400 includes an x-axis guiderail 411 and a y-axis guiderail 412 so as to move the support bracket 410 in x-axis and y-axis, and in this case, it is preferable that the x-axis guiderail 411 and the y-axis guiderail 412 make moving in the horizontal direction more efficient by fixing support bracket 410 to an upper side of one guiderail so as to easily control the position of the support bracket 410 and move the guiderail to which the support bracket 410 is fixed along the other guiderail.

In FIG. 3, the plotter 100 is provided at the right side of the support bracket 410, the electrospinning unit 200 is provided at the left side of the support bracket 410, the support bracket 410 is moved while being fixed to the x-axis guiderail 411, the x-axis guiderail 411 is fixed to the y-axis guiderail 412, but each constitution may be variously deformed according to the necessity.

In addition, in the case where the support bracket 410 is fixed to the x-axis guiderail 411, a rotation means 414 may be formed so as to rapidly determine a ejecting means (plotter 100 or electrospinning unit 200) by rotation.

That is, the cell culture scaffold manufacturing apparatus 700 of the exemplary embodiment has merits that the cell culture scaffold is easily formed by ejecting biopolymer solution performed through the plotter 100, and rotating the electrospinning unit 200 to the position of the plotter 100 using the rotation means 414 by 180°, or moving the support bracket 410 in the y-axis direction in the drawing.

In the drawing, the plotter 100 is formed at a side of the support bracket 410, and the electrospinning unit 200 is formed at the other side opposite thereto, but the cell culture scaffold manufacturing apparatus 700 of the exemplary embodiment has the electrospinning unit 200 that is not an essential constitution but an additional constitution of the plotter 100 and the cylindrical collection portion 300, and the form where the electrospinning unit 200 is not formed may also be within the scope of the present invention.

The cell culture scaffold manufacturing apparatus 700 of the exemplary embodiment includes a collecting position control portion 500 controlling the rotation speed of the cylindrical collection portion 300.

The collecting position control portion 500 is a means determining the position at which the solution ejected through the plotter nozzle 120 of the plotter 100 and the electrospinning nozzle 220 of the electrospinning unit 200 is collected by controlling the rotation speed of the cylindrical collection portion 300.

The collecting position control portion 500 may include a fixing shaft 510 fixing the cylindrical collection portion 300 and a driver 520 rotating the fixing shaft 510.

The driver 520 may be connected to the fixing shafts 510 at both sides to which the cylindrical collection portion 300 is fixed, and may be connected to only a side of the fixing shaft 510.

The driver 520 is a means rotating the cylindrical collection portion 300 by rotating the fixing shaft 510, and a means rotating in one direction and both directions according to the necessity is used.

Figure 5:
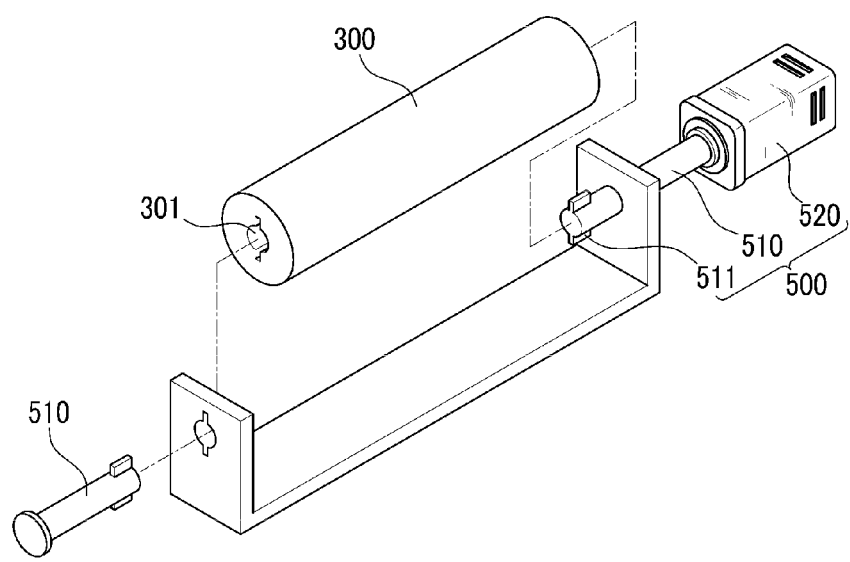
FIG. 5 is an exploded perspective view that illustrates a second position control portion of a cell culture scaffold manufacturing apparatus according to the first exemplary embodiment of the present invention.

FIG. 5 is an exploded perspective view that illustrates a collecting position control portion of a cell culture scaffold manufacturing apparatus according to the first exemplary embodiment of the present invention.

The cylindrical collection portion 300, as shown in FIG. 5, is provided with a hollow portion 301 into which the fixing shaft 510 is inserted in a central-axis direction at both ends thereof so as to be detachably connected with the fixing shaft 510 of the collecting position control portion 500.

The cylindrical collection portion 300 should collect the cell culture scaffold formed through the plotter 100 and the electrospinning unit 200, and since various cylindrical collection portion 300 may be used according to the diameter of the cell culture scaffold, the cylindrical collection portion 300 is detachably formed in the fixing shaft 510.

Accordingly, the cylindrical collection portion 300 may be provided with the hollow portion 301 having the same size and shape or a plurality of hollow portions 301 having different diameters, and may be selectively used according to the interior diameter of the manufactured cell culture scaffold.

Figure 6:
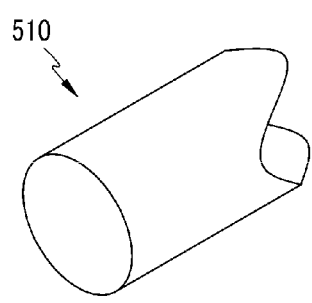
FIG. 6 a perspective view illustrating various modified examples of a fixing shaft applied to the cell culture scaffold manufacturing apparatus according to the first exemplary embodiment of the present invention.
Figure 6:
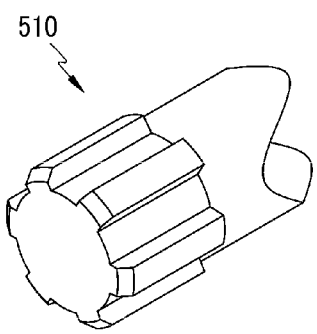
Figure 6:
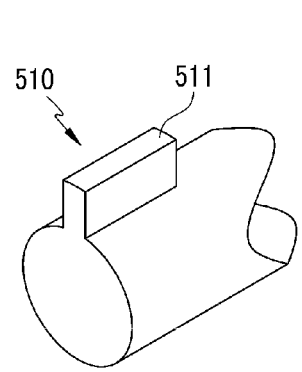
Figure 6:
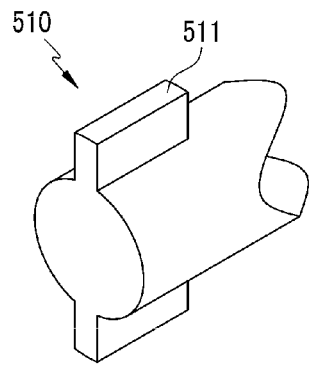

FIG. 6 a perspective view illustrating various modified examples of a fixing shaft applied to the cell culture scaffold manufacturing apparatus according to the first exemplary embodiment of the present invention. Shapes of the fixing shaft 510 and the hollow portion 301 corresponding thereto may be various, and FIG. 6 illustrates modified examples thereof and the shape of the fixing shaft 510.

FIG. 6(a) illustrates a cylindrical fixing shaft 510, and FIG. 6(b) illustrates an example of prevention of idle rotation of a sawtooth type fixing shaft 510.

FIGS. 6(c) and (d) illustrate an example of formation of the position determination protrusion portion 511 in the cylindrical fixing shaft 510 shown in FIG. 6(a), FIG. 6(c) illustrates an example of formation of one position determination protrusion portion 511 at both sides thereof and FIG. 6(d) illustrates an example of formation of two position determination protrusion portions 511 at both sides thereof.

The position determination protrusion portion 511 determines the collection position of the cylindrical collection portion 300 by determining the fastening position with the cylindrical collection portion 300, and in this case, of course, the hollow portion 301 corresponds to the shape of the fixing shaft 510.

The cell culture scaffold manufacturing apparatus 700 of the exemplary embodiment may manufacture various cell culture scaffolds by controlling the plotting position control portion 400 and the collecting position control portion 500, which is controlled by a controller.

Figure 7:
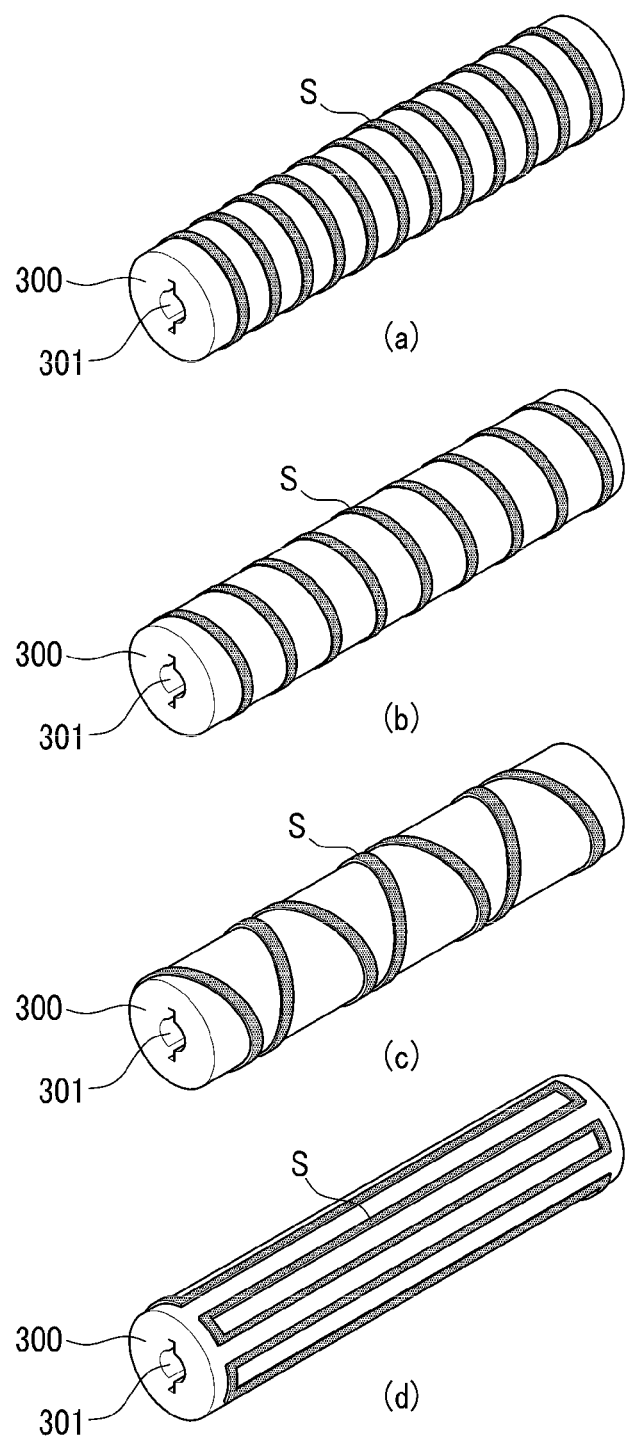
FIG. 7 is a view that illustrates various shapes of the cell culture scaffold manufactured by cell culture scaffold manufacturing apparatus according to the first exemplary embodiment of the present invention.

FIG. 7 is a view that illustrates various shapes of the cell culture scaffold S manufactured by cell culture scaffold manufacturing apparatus 700 according to the first exemplary embodiment of the present invention.

FIG. 7(a) illustrates an example where a ring shape is formed by repeating a process for performing rotating using the collecting position control portion 500 while the material for forming the cell culture scaffold is ejected through the plotter nozzle 120 by 360°, stopping the ejecting, moving the position of the plotter nozzle 120 by moving the support bracket 410 along the x-axis guiderail 411, and performing the ejecting while the collecting position control portion 500 is rotated again.

FIG. 7(b) illustrates an example where a spiral shape is formed by performing rotation using the collecting position control portion 500 while the material for forming the cell culture scaffold is ejected through the plotter nozzle 120 and moving the position of the plotter nozzle 120 by moving the support bracket 410 along the x-axis guiderail 411.

FIG. 7(c) illustrates an example where a continuous shape is formed by repeating a process for moving the position of the plotter nozzle 120 by moving the support bracket 410 along the x-axis guiderail 411 while ejecting is performed through the plotter nozzle 120, performing rotation at a predetermined angle by using the collecting position control portion 500, moving the position of the plotter nozzle 120 in an opposite direction by moving the support bracket 410 in the opposite direction the x-axis guiderail 411, and performing rotation at a predetermined angle again.

In FIG. 7(c), when the collecting position control portion 500 is rotated, in the case where the ejecting is stopped, a discontinuous shape may be manufactured in only a length direction of the cylindrical collection portion 300.

FIG. 7(d) illustrates an example where a zigzag shape is formed by moving the position of the plotter nozzle 120 by moving the support bracket 410 along the x-axis guiderail 411 while the collecting position control portion 500 is positively and negatively rotated at a predetermined angle.

The cell culture scaffold manufacturing apparatus 700 of the exemplary embodiment, in addition to the shapes shown in FIG. 7(a) to (d), may form more various types of cell culture scaffold S by controlling the plotting position control portion 400 and the collecting position control portion 500 through the controller, and the combined shape of the above shapes can be manufactured.

The cell culture scaffold S of the exemplary embodiment is manufactured by the cell culture scaffold manufacturing apparatus 700 having the above characteristics, and may be used in all cylindrical human body tissues including a vascular, a nervous conduit and a trachea. In addition, the cell culture scaffold S of the exemplary embodiment may be used for various medical goods in addition to the above human body tissue. Particularly, the cell culture scaffold S of the exemplary embodiment may be used as a stent having a cylindrical net shape used in order to extend a contracted vascular.

The cylindrical shape of the cell culture scaffold S of the exemplary embodiment includes, in views of a side thereof, a complete cylinder shape, and the cell culture scaffolds S having only a predetermined region of the cylindrical shape by using the cylindrical collection portion 300.

There are merits in that the cell culture scaffold S of the exemplary embodiment can easily form a cell culture scaffold S by using the plotter 100 ejecting the solution in which the biodegradable material is dissolved or melted, can form a nano-scale cell culture scaffold S by forming the electrospinning unit 200 electrospinning the biopolymer solution in one apparatus and performing simultaneous moving, can increase manufacturing efficiency by reducing a manufacturing time, and can improve cell proliferation efficiency.

Figure 8:
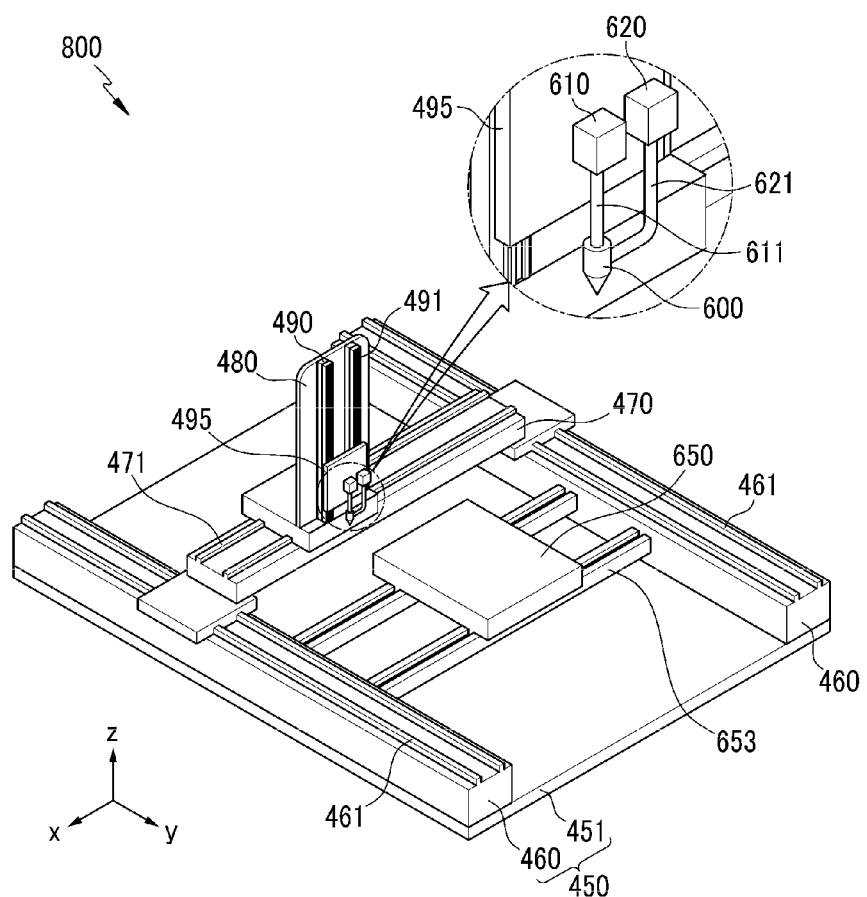
FIG. 8 is a perspective view that illustrates a cell culture scaffold manufacturing apparatus according to a second exemplary embodiment of the present invention.
Figure 9:
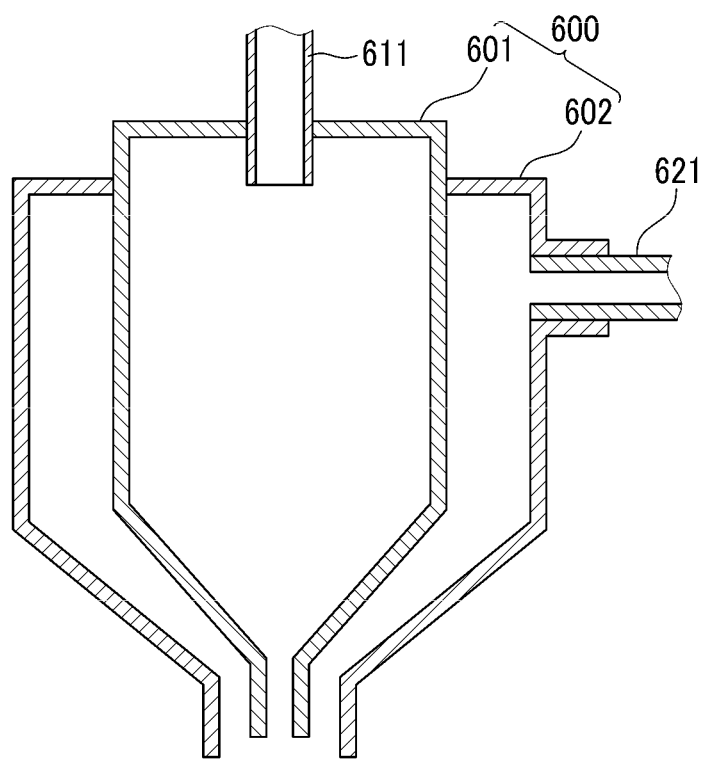
FIG. 9 is a cross-sectional view that illustrates a double spray nozzle of a cell culture scaffold manufacturing apparatus according to the second exemplary embodiment of the present invention.

FIG. 8 is a perspective view that illustrates a cell culture scaffold manufacturing apparatus according to a second exemplary embodiment of the present invention, and FIG. 9 is a cross-sectional view that illustrates a double ejection nozzle of a cell culture scaffold manufacturing apparatus according to the second exemplary embodiment of the present invention.

Referring to FIGS. 8 and 9, the cell culture scaffold manufacturing apparatus 800 of the exemplary embodiment includes a base frame 450, and the base frame 450 includes a lower plate 451 and a y-axis guiderail support 460. The y-axis guiderail supports 460 may be a straight type of block, and may be separated from each other at both ends of the lower plate 451 and protrude upwards. The y-axis guiderails 461 are installed on the y-axis guiderail supports 460.

The x-axis guiderail support 470 is movably mounted in a y-axis direction on the y-axis guiderail 461. In this case, an end of the x-axis guiderail support 470 is mounted on one side y-axis guiderail 461, and the other end of the x-axis guiderail support 470 is mounted on the other y-axis guiderail 461. Meanwhile, the x-axis guiderail 471 is installed on an upper surface of the x-axis guiderail support 470.

A support bracket 480 is movably mounted on the x-axis guiderail 471 in an x-axis direction. The support bracket 480 includes a vertical plate that is disposed in a z-axis direction. A z-axis guiderail support 490 is installed in the support bracket 480. The z-axis guiderail support 490 is fixed to the vertical plate of the support bracket 480.

Meanwhile, the z-axis guiderail 491 is installed on the z-axis guiderail support 490. A z-axis moving bracket 495 is movably mounted on the z-axis guiderail 491 in the z-axis direction. A drug storage portion 610 and a solution storage portion 620 are fixed to an external surface of the z-axis moving bracket 495.

The drug storage portion 610 is a tank in which a drug, and the solution storage portion 620 is a tank in which the biopolymer solution forming the cell culture scaffold is stored. A water-soluble or biodegradable material for forming a pore in the cell culture scaffold may be further added to the solution storage portion 620.

The cell culture scaffold manufacturing apparatus 800 includes a first supply tube 611 connected to the drug storage portion 610 and a second supply tube 621 connected to the solution storage portion 620, the other end of the first supply tube 611 into which the drug is supplied is connected to a first plotter nozzle 601, and the second supply tube 621 to which a synthetic polymer is supplied is connected to a second plotter nozzle 602. As shown in FIG. 9, the plotter 600 having the double ejection nozzle structure is formed of the first plotter nozzle 601 and the second plotter nozzle 602, and the second plotter nozzle 602 is formed of a cylinder tube while surrounding an external surface of the first plotter nozzle 601 in a length direction.

A collection table 650 is installed between the y-axis guiderail supports 460. The collection table 650 is a table in which a drug, a synthetic polymer, and, a water-soluble or biodegradable material sprayed through the plotter 600 are plotted.

The collection table 650 may be movably mounted on the auxiliary guiderail 653 in the y-axis direction. In this case, an end of the auxiliary guiderail 653 may be connected to a side of the y-axis guiderail support 460, and the other end of the auxiliary guiderail 653 may be connected to the other side of the y-axis guiderail support 460.

The cell culture scaffold may be manufactured by using the cell culture scaffold manufacturing apparatus 800, first, the drug is supplied to the drug storage portion 610, a synthetic polymer for forming the cell culture scaffold is supplied to the solution storage portion 620, and a water-soluble or biodegradable material for forming a pore is added to the solution storage portion 620. After the drug is provided through the first supply tube 611 into the first plotter nozzle 630, the synthetic polymer and the water-soluble or biodegradable material are provided through the second supply tube 621 into the second plotter nozzle 640, and the cell culture scaffold may be manufactured by performing plotting by using the cell culture scaffold manufacturing apparatus 800.

Figure 10:
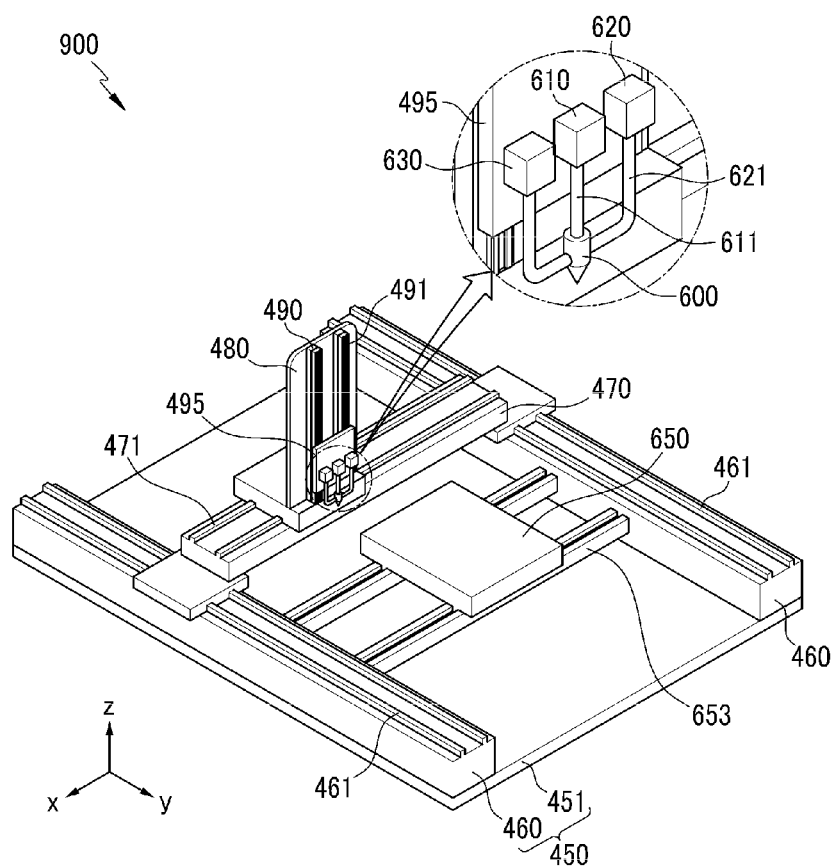
FIG. 10 is a perspective view that illustrates a cell culture scaffold manufacturing apparatus according to a third exemplary embodiment of the present invention.
Figure 11:
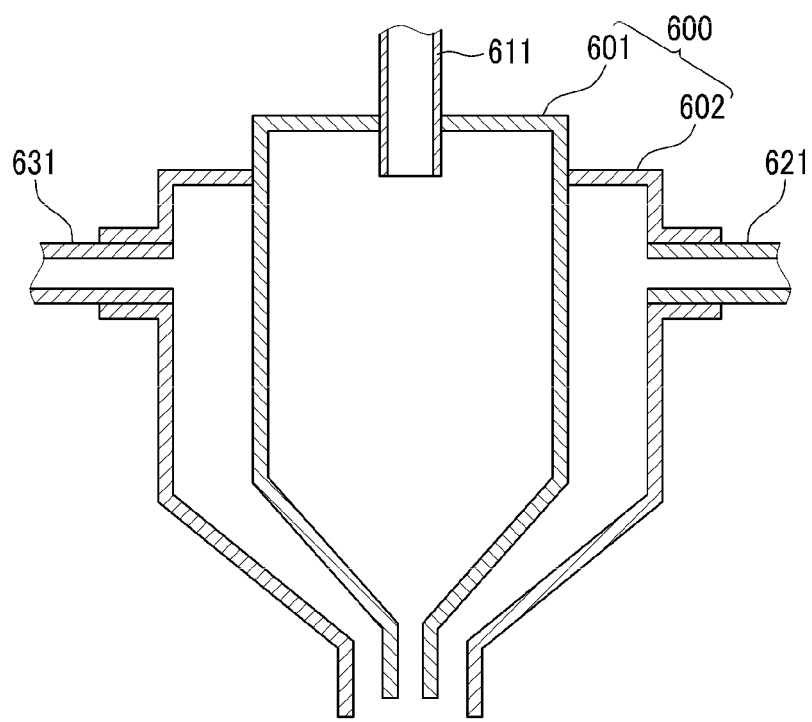
FIG. 11 is a cross-sectional view that illustrates a double spray nozzle of a cell culture scaffold manufacturing apparatus according to the third exemplary embodiment of the present invention.

FIG. 10 is a perspective view that illustrates a cell culture scaffold manufacturing apparatus 900 according to a third exemplary embodiment of the present invention, and FIG. 11 is a cross-sectional view that illustrates a double ejection nozzle of a cell culture scaffold manufacturing apparatus 900 according to the third exemplary embodiment of the present invention.

Referring to FIG. 10 and FIG. 11, a drug storage portion 610, a solution storage portion 620 and an additive storage portion 630 are fixed to an external surface of the z-axis moving bracket 495.

The drug storage portion 610 is a tank in which the drug is stored, the solution storage portion 620 is a tank in which the synthetic polymer for forming the cell culture scaffold is stored, and the additive storage portion 630 is a tank in which the water-soluble or biodegradable material for forming the pore in the cell culture scaffold is stored.

The cell culture scaffold manufacturing apparatus 900 includes the first supply tube 611 connected to the drug storage portion 610, the second supply tube 621 connected to the solution storage portion 620, and the third supply tube 631 connected to the additive storage portion 630, the other end of the first supply tube 611 into which a drug is supplied is connected to the first plotter nozzle 601, and the second supply tube 621 to which a synthetic polymer is supplied and the third supply tube 631 to which an additive is supplied are connected to the second plotter nozzle 602. The plotter 600 having the double spray nozzle structure is formed of the first plotter nozzle 601 and the second plotter nozzle 602, and the second plotter nozzle 602 is formed of a ring-shaped tube while surrounding an external surface of the first plotter nozzle 601 in a length direction.

A collection table 650 is installed between the y-axis guiderail supports 460. The collection table 650 is a table in which a drug, a synthetic polymer, and, a water-soluble or biodegradable material sprayed through the plotter 600 is plotted.

The collection table 650 may be movably mounted on the auxiliary guiderail 653 in the x-axis direction. In this case, an end of the auxiliary guiderail 653 may be connected to a side of the y-axis guiderail support 460, and the other end of the auxiliary guiderail 653 may be connected to the other side of the y-axis guiderail support 460.

The cell culture scaffold according to the exemplary embodiment may be manufactured by using the cell culture scaffold manufacturing apparatus 900, first, a drug is supplied to the drug storage portion 610, a synthetic polymer for forming the cell culture scaffold is supplied to the solution storage portion 620, and a water-soluble or biodegradable material for forming a pore is added to the additive storage portion 630. After the drug is provided through the first supply tube 611 into the first plotter nozzle 601, the synthetic polymer is provided through the second supply tube 621 into the second plotter nozzle 602, and the water-soluble or biodegradable material is provided through the third supply tube 631 into the second plotter nozzle 602, and the cell culture scaffold may be manufactured by performing plotting by using the cell culture scaffold manufacturing apparatus 900.

Figure 12:
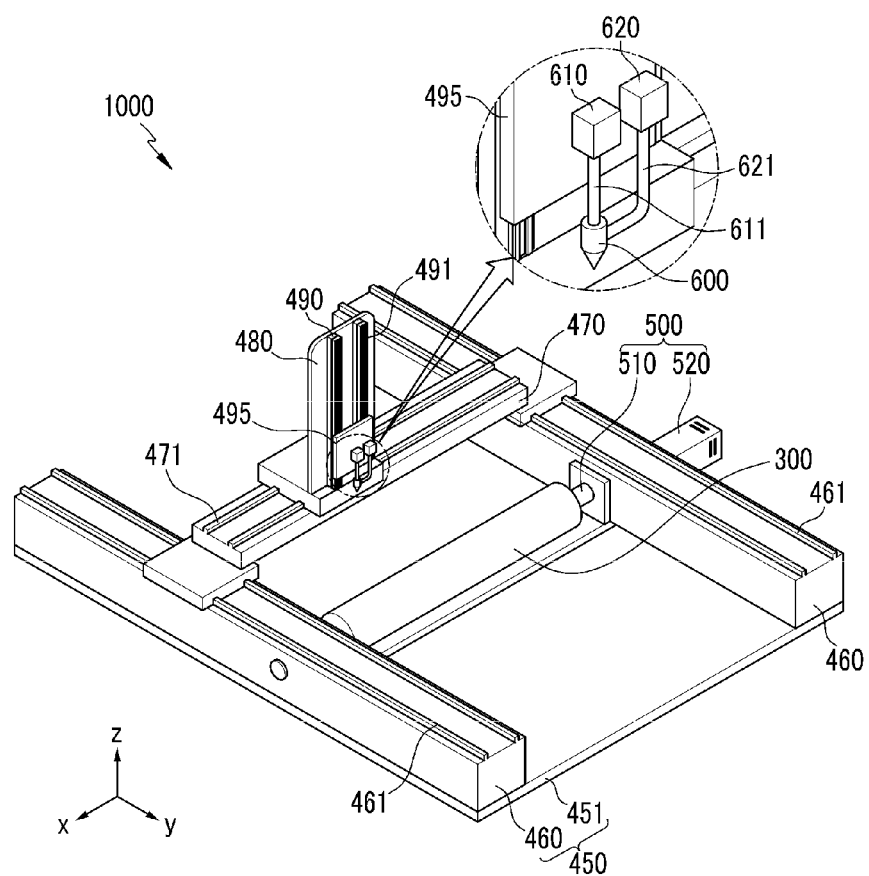
FIG. 12 is a perspective view that illustrates a cell culture scaffold manufacturing apparatus according to a fourth exemplary embodiment of the present invention.

FIG. 12 is a perspective view that illustrates a cell culture scaffold manufacturing apparatus 1000 according to a fourth exemplary embodiment of the present invention.

The cell culture scaffold manufacturing apparatus 1000 according to the exemplary embodiment, like the cell culture scaffold manufacturing apparatus 800 according to the second exemplary embodiment, includes a base frame 450, and the base frame 450 includes a lower plate 451 and a y-axis guiderail support 460. The y-axis guiderail supports 460 may be a straight type of block, and may be separated from each other at both ends of the lower plate 451 and protrude upwards. The y-axis guiderails 461 are installed on the y-axis guiderail supports 460.

The x-axis guiderail support 470 is movably mounted in a y-axis direction on the y-axis guiderail 461. In this case, an end of the x-axis guiderail support 470 is mounted on a y-axis guiderail 461, and the other end of the x-axis guiderail support 470 may be mounted on the other y-axis guiderail 461. Meanwhile, the x-axis guiderail 471 is installed on an upper surface of the x-axis guiderail support 470.

A support bracket 480 is movably mounted on the x-axis guiderail 471 in an x-axis direction. The support bracket 480 includes a vertical plate that is disposed in a z-axis direction. A z-axis guiderail support 490 is installed in the support bracket 480. The z-axis guiderail support 490 is fixed to the vertical plate of the support bracket 480.

Meanwhile, the z-axis guiderail 491 is installed on the z-axis guiderail support 490. A z-axis moving bracket 495 is movably mounted on the z-axis guiderail 491 in the z-axis direction. A drug storage portion 610 and a solution storage portion 620 are fixed to an external surface of the z-axis moving bracket 495.

The drug storage portion 610 is a tank in which a drug is stored, and the solution storage portion 620 is a tank in which the synthetic polymer forming the cell culture scaffold is stored. A water-soluble or biodegradable material for forming a pore in the cell culture scaffold may be further added to the solution storage portion 620.

The cell culture scaffold manufacturing apparatus 1000 includes the first supply tube 611 connected to the drug storage portion 610 and the second supply tube 621 connected to the solution storage portion 620, the other end of the first supply tube 611 into which a drug is supplied is connected to the first plotter nozzle 601, and the second supply tube 621 to which a synthetic polymer is supplied is connected to the second plotter nozzle 602. The plotter 600 having the double spray nozzle structure is formed of the first plotter nozzle 601 and the second plotter nozzle 602, and the second plotter nozzle 602 is formed of a ring-shaped tube while surrounding an external surface of the first plotter nozzle 601 in a length direction.

Meanwhile, the cell culture scaffold manufacturing apparatus 1000 according to the exemplary embodiment installs a cylindrical collection portion 300 between the y-axis guiderails 461. The cylindrical collection portion 300 forms the cell culture scaffold by plotting the drug, the synthetic polymer and the water-soluble or biodegradable material sprayed through the plotter 600.

The cylindrical collection portion 300 applied to the exemplary embodiment may have all characteristics of the cylindrical collection portion 300 of the cell culture scaffold manufacturing apparatus 700 of the first exemplary embodiment.

The cell culture scaffold manufacturing apparatus 1000 includes a collecting position control portion 500 controlling the rotation speed of the cylindrical collection portion 300. The collecting position control portion 500 is a means determining the position at which the solution ejected through the plotter nozzle 120 of the plotter 100 is collected by controlling the rotation speed of the cylindrical collection portion 300.

The collecting position control portion 500 may include a fixing shaft 510 fixing the cylindrical collection portion 300 and a driver 520 rotating the fixing shaft 510. The driver 520 may be connected to the fixing shafts 510 at both sides to which the cylindrical collection portion 300 is fixed, and may be connected to only a side of the fixing shaft 510. The driver 520 is a means rotating the cylindrical collection portion 300 by rotating the fixing shaft 510, and a means rotating in one direction and both directions according to the necessity is used.

In another exemplary embodiment, like the cell culture scaffold manufacturing apparatus 900 according to the third exemplary embodiment, a drug storage portion 610, a solution storage portion 620 and an additive storage portion 630 are fixed to the external surface of the z-axis moving bracket 495, and like the cell culture scaffold manufacturing apparatus 700 according to the first exemplary embodiment, the cylindrical collection portion 300 may be installed, which belongs to the scope of the present invention.

Hereinafter, the method for manufacturing the cell culture scaffold according to the fifth exemplary embodiment of the present invention using the cell culture scaffold manufacturing apparatus 800 according to the second exemplary embodiment of the present invention shown in FIGS. 8 and 9 will be stepwisely described in detail.

The method for manufacturing the cell culture scaffold according to the exemplary embodiment includes a first step for supplying a drug that promotes a cell growth to a drug storage portion 610, supplying a synthetic polymer solution used as the scaffold to a solution storage portion 620, and supplying a water-soluble or biodegradable material generating pores to the solution storage portion 620; and a second step for providing the drug of the first step through the first supply tube 611 to the first plotter nozzle 601, providing the synthetic polymer and the water-soluble or biodegradable material through the second supply tube 621 into the second plotter nozzle 602, and performing plotting by using the plotter 600.

The drug of the first step may promote the cell growth, and use a growth factor, cytokine, an antibiotic, and an antimicrobial may be used. In more detail, as the growth factor, a bone morphogenetic protein (BMP), a cell proliferation suppress factor (TGF-β), an insulin-like growth factor (IGF), a fibroblast growth factor (FGF), a platelet-derived growth factor (PDGF), keratinocyte cell growth factor (KGF) or an epidermal growth factor (EGF) may be used, as the cytokine, interleukin-2, interferon-α (IFN-α) or interferon-β (IFN-β) may be used, as the antibiotic, one or more selected from the group consisting of penicillin, streptomycin, kanamycin, neomycin, bacitracin, gentamycin and vancomycin may be used, and as the antimicrobial, amphotericin-B, nystatin, or polymixin may be used. The drug may include a cell or may not include the cell.

In addition, the synthetic polymer of the first step may be used as the scaffold, and one or two or more selected from the group consisting of polycaprolactone, polylactide, polyglycolide, and polydioxanone may be used.

In addition, the material added to the solution storage portion 620 in the first step is a water-soluble material or a biodegradable material having a rapid biodegradable speed, and since the pore generated when the cell culture scaffold is dipped in water can be controlled by controlling a component of the water-soluble material or the biodegradable material, a discharge amount of the drug may be controlled. As the water-soluble material, a salt solution, sucrose, polyethylene oxide (PEO) or polyvinyl alcohol (PVA) may be used, and as the biodegradable material, a polyglycolic acid, polycaprolactone, a polylactic acid or polydioxanone may be used.

Hereinafter, the method for manufacturing the cell culture scaffold according to the sixth exemplary embodiment of the present invention using the cell culture scaffold manufacturing apparatus 900 according to the third exemplary embodiment of the present invention shown in FIGS. 10 and 11 will be stepwisely described in detail.

The method for manufacturing the cell culture scaffold according to the exemplary embodiment includes step A for supplying a drug that promotes a cell growth to a drug storage portion 610, supplying a synthetic polymer used as the scaffold to a solution storage portion 620, and supplying a water-soluble or biodegradable material generating pores to the additive storage portion 630; and step B for providing the drug of step A through the first supply tube 611 to the first plotter nozzle 601, providing the synthetic polymer and the water-soluble or biodegradable material through the second supply tube 621 and the third supply tube 631 into the second plotter nozzle 602, and performing plotting by using the plotter 600.

The drug of step A may use a growth factor, cytokine, an antibiotic, and an antimicrobial may be used. In more detail, as the growth factor, a bone morphogenetic protein (BMP), a cell proliferation suppress factor (TGF-β), an insulin-like growth factor (IGF), a fibroblast growth factor (FGF), a platelet-derived growth factor (PDGF), keratinocyte cell growth factor (KGF) or an epidermal growth factor (EGF) may be used, as the cytokine, interleukin-2, interferon-α(IFN-α) or interferon-β (IFN-β) may be used, as the antibiotic, one or more selected from the group consisting of penicillin, streptomycin, kanamycin, neomycin, bacitracin, gentamycin and vancomycin may be used, and as the antimicrobial, amphotericin-B, nystatin, or polymixin may be used. The drug may include a cell or may not include the cell.

In addition, the synthetic polymer of step A may be one or more selected from the group consisting of polycaprolactone, polylactide, polyglycolide, and polydioxanone.

In addition, as the water-soluble material of step A, a salt solution, sucrose, polyethylene oxide (PEO) or polyvinyl alcohol (PVA) may be used, and as the biodegradable material, a polyglycolic acid, polycaprolactone, a polylactic acid or polydioxanone may be used.

Hereinafter, the method for manufacturing the cell culture scaffold according to the seventh exemplary embodiment of the present invention using the cell culture scaffold manufacturing apparatus 1000 according to the fourth exemplary embodiment of the present invention shown in FIG. 12 will be described.

The method for manufacturing the cell culture scaffold according to the exemplary embodiment includes supplying drugs that promotes a cell growth to the drug storage portion 610, supplying synthetic polymer solution to the solution storage portion 620, and supplying a water-soluble or biodegradable material generating pores to the solution storage portion 620; and providing the drug through the first supply tube 611 to the first plotter nozzle 601, providing the synthetic polymer solution and the water-soluble or biodegradable material through the second supply tube 621 into the second plotter nozzle 602, and then performing plotting by using the plotter 600.

The drugs may be the same kind of the drugs that are supplied in the fifth embodiment, and synthetic polymer solution and additive material supplied to the solution storage portion 620 may be the same kind of the synthetic polymer solution and additive material supplied in the fifth embodiment.

The plotter 600 may be moved in x-y-z axis direction to control the position of ejecting, thereby plotting a cell culture scaffold having a predetermined shape.

The collecting position control portion 500 determines the position at which the solution ejected through the plotter 600 is collected by controlling the rotation speed of the cylindrical collection portion 300.

Since the cell culture scaffold manufactured according to the method for manufacturing the cell culture scaffold according to the fifth through the seventh exemplary embodiments of the present invention keeps the drug including the water-soluble or the biodegradable material and the drug is slowly released in a controlled release form through the pores generated by dissolving or biologically degrading the water-soluble or the biodegradable material, the pores may be controlled by controlling the amount of the water-soluble or biodegradable material, and, as a result, a drug efflux may be controlled.

Figure 13:
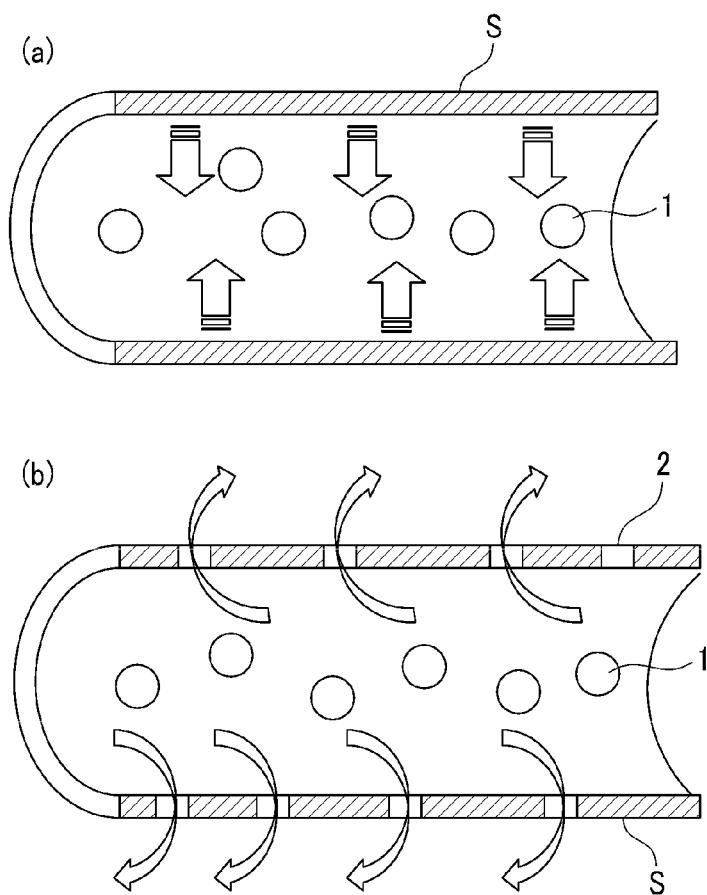
FIG. 13 is a schematic view that illustrates a drug efflux generated in the cell culture scaffold manufactured according to an exemplary embodiment of the present invention.

FIG. 13 is a schematic view that illustrates a drug efflux generated in the cell culture scaffold according to a seventh exemplary embodiment of the present invention, while showing cross-section of the cell culture scaffold S. As shown in FIG. 13(a), it can be seen that a drug 1 is included in the cell culture scaffold S, and is controlled in a controlled release form, and as shown in FIG. 13(b), a pore 2 is generated by dissolving or biologically degrading the water-soluble or the biodegradable material and the drug 1 is discharged therethrough.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A cell culture scaffold manufacturing apparatus for manufacturing a cell culture scaffold that is used in regeneration of a tissue, the apparatus comprising:
   a plotter that includes a first solution storage portion in which a biopolymer solution is stored, and a plotter nozzle for ejecting a solution supplied from the first solution storage portion; an electrospinning unit that electrospins nanofibers;
   a plotting position control portion that controls a plotting position by moving the plotter and the electrospinning unit in an x-y-z axis direction; a cylindrical collection portion that has a cylinder shape for forming a cylindrical cell culture scaffold and is disposed at a lower portion of the plotter so that the solution ejected through the plotter nozzle of the plotter is collected; a collecting position control portion that controls a position at which the solution is collected by controlling a rotation speed of the cylindrical collection portion; and a controller that controls the plotting position control portion and the collecting position control portion,
   wherein the plotting position control portion includes a support bracket that supports the plotter and the electrospinning unit, the plotter is provided at one side of the support bracket and the electrospinning unit is provided at another side of the support bracket, the support bracket includes a rotation means that rotates the electrospinning unit to the position of the plotter, the collecting position control portion includes a fixing shaft fixing the cylindrical collection portion and a driver rotating the fixing shaft, and the cylindrical collection portion is detachably formed in the fixing shaft by forming a hollow portion into which the fixing shaft is inserted at both ends in a central axis direction, so that various cylindrical collection portion as a framework for forming the cylindrical cell culture scaffold can be used according to the diameter of the cylindrical cell culture scaffold; wherein the plotting position control portion includes a x-axis guiderail and y-axis guiderail moving the support bracket in a x-axis direction and a y-axis direction, respectively, and the support bracket includes a z-axis guiderail for moving the plotter and the electrospinning unit in a z-axis direction.

2. The apparatus of claim 1, wherein:
   the fixing shaft includes a position determination protrusion portion in which a portion of an external circumferential surface is protruded to determine a collection position of the cylindrical collection portion,
   a hollow region of the hollow portion is extended so that the position determination protrusion portion is inserted thereinto.

3. The apparatus of claim 1, wherein:
   the electrospinning unit includes a second solution storage portion in which a biopolymer solution is stored, an electrospinning nozzle that electrospins a solution supplied from the second solution storage portion, and a voltage generation portion applying a voltage to the electrospinning nozzle and the cylindrical collection portion,
   wherein the nanofibers are electrospun between the cell culture scaffolds formed through the plotter by using the electrospinning unit.

4. The apparatus of claim 1, wherein:
   the plotter includes a first plotter nozzle and a second plotter nozzle having divided regions,
   the cell culture scaffold manufacturing apparatus further includes a drug storage portion connected to the first plotter nozzle through a first supply tube, and the solution storage portion connected to the second plotter nozzle through a second supply tube.

5. The apparatus of claim 4, wherein:
   the second plotter nozzle surrounds an external side of the first plotter nozzle in a length direction and has a ring-shaped tube.

6. The apparatus of claim 4, further comprising:
   an additive storage portion connected to the first plotter nozzle through the third supply tube.

* * * * *